United States Patent [19]
Bracken et al.

[11] Patent Number: 5,922,470
[45] Date of Patent: Jul. 13, 1999

[54] SOFT POLYSILOXANES HAVING A PRESSURE SENSITIVE ADHESIVE

[75] Inventors: Ronald L. Bracken, Memphis; Gerald R. Dever, Cordova; Ronald M. Feret, Bartlett; Daniel B. Snyder, Memphis, all of Tenn.

[73] Assignee: Schering-Plough HealthCare Products, Inc., Memphis, Tenn.

[21] Appl. No.: 08/451,295

[22] Filed: May 26, 1995

Related U.S. Application Data

[63] Continuation of application No. PCT/US94/14164, Dec. 19, 1994, which is a continuation-in-part of application No. 08/171,799, Dec. 22, 1993, abandoned.

[51] Int. Cl.$^6$ .................................................. B32B 9/04
[52] U.S. Cl. ...................... 428/447; 427/575; 427/597; 523/213; 524/862; 528/15
[58] Field of Search ............................... 528/15; 523/213; 524/862; 427/575, 577; 428/447

[56] References Cited

U.S. PATENT DOCUMENTS

| | | |
|---|---|---|
| 1,001,161 | 8/1911 | Packard . |
| 1,080,303 | 12/1913 | Scholl . |
| 1,580,170 | 4/1926 | Scholl . |
| 2,556,887 | 6/1951 | Ryan . |
| 2,641,066 | 6/1953 | Filardo . |

(List continued on next page.)

FOREIGN PATENT DOCUMENTS

| | | |
|---|---|---|
| 0091737 A3 | 10/1983 | European Pat. Off. . |
| 0 489518A1 | 10/1992 | European Pat. Off. . |
| 2225480 | 11/1974 | France . |
| 2620933 | 3/1989 | France . |
| 2660168 | 10/1991 | France . |
| PCT/US93/ 06111 | 1/1994 | WIPO . |

OTHER PUBLICATIONS

American Society For Testing and Materials (ASTM) Designation: D2979–71 (Reapproved 1982), Standard Test Method for Pressure–Sensitive Tack of Adhesives Using an Inverted Probe Machine, pp. 187–189, from the Annual Book of ASTM Standards, vol. 15.09.

Tack Rolling Ball: Test Methods for Pressure Sensitive Tapes, 9th Edition, PSTC–6, revised Aug., 1989, pp. 33–34.

ASTM Designation:E96–80, Standard Test Methods for Water Vapor Transmission of Materials, edited May 1987, pp. 629–633.

S.R. Gaboury and M.W. Urban, The Effect of Chloro–Functional Molecules on the Ammonia Plasma Treatment of Silicone Elastomers, J.Applied Polymer Science, vol. 44, (1992), pp. 401–407.

M.W. Urban and M.T. Stewart, DMA and ATR FT–IR Studies of Gas Plasma Modified Silicone Elastomer Surfaces, J. Applied Polymer Science, vol., 39, (1990), pp. 265–283.

S.R. Gaboury and M.W. Urban, Spectroscopic evidence for Si–H formation during microwave plasma modification of poly(dimethylsiloxane)elastomer surfaces, Polym. Commun., 32(13), (1991), pp. 390–392.

H.J. Hettlich et al., Plasma–induced surface modifications on silicone intraocular lenses: chemical analysis and in vitro characterization, Biomaterials 12(5), (1991), pp. 521–524.

(List continued on next page.)

*Primary Examiner*—James J. Bell
*Attorney, Agent, or Firm*—Joseph T. Majka

[57] ABSTRACT

An article comprising a soft, polysiloxane elastomer having a hardness of 5–55 durometer units (Shore 00), the elastomer having a pressure sensitive adhesive on at least one of its surfaces is described. A process for bonding a pressure sensitive adhesive to the soft polysiloxane elastomeric is also described.

10 Claims, 1 Drawing Sheet

U.S. PATENT DOCUMENTS

| | | |
|---|---|---|
| 3,186,006 | 6/1965 | Miller . |
| 3,213,048 | 10/1965 | Boot . |
| 3,220,972 | 11/1965 | Lamoreaux . |
| 3,247,845 | 4/1966 | Kennedy . |
| 3,253,600 | 5/1966 | Scholl . |
| 3,253,601 | 5/1966 | Scholl . |
| 3,445,420 | 5/1969 | Kookootsedes et al. . |
| 3,548,420 | 12/1970 | Spence . |
| 3,594,813 | 7/1971 | Sanderson . |
| 3,635,743 | 1/1972 | Smith . |
| 3,663,973 | 5/1972 | Spence . |
| 3,692,023 | 9/1972 | Philips et al. . |
| 3,723,497 | 3/1973 | Baney . |
| 3,839,246 | 10/1974 | Hamilton, Jr. et al. . |
| 3,862,869 | 1/1975 | Peterson et al. . |
| 3,880,155 | 4/1975 | Rosoff . |
| 3,884,866 | 5/1975 | Jeram et al. . |
| 3,957,713 | 5/1976 | Jeram et al. . |
| 4,019,209 | 4/1977 | Spence . |
| 4,061,609 | 12/1977 | Bobear . |
| 4,101,499 | 7/1978 | Herzig . |
| 4,162,243 | 7/1979 | Lee et al. . |
| 4,189,546 | 2/1980 | Deichert et al. . |
| 4,247,577 | 1/1981 | Imada et al. . |
| 4,322,320 | 3/1982 | Caprino . |
| 4,332,844 | 6/1982 | Hamada et al. . |
| 4,413,359 | 11/1983 | Akiyama et al. . |
| 4,460,739 | 7/1984 | Ashby . |
| 4,573,216 | 3/1986 | Wortberg . |
| 4,601,286 | 7/1986 | Kaufman . |
| 4,623,593 | 11/1986 | Baier et al. . |
| 4,655,210 | 4/1987 | Edenbaum et al. . |
| 4,660,553 | 4/1987 | Naylor et al. . |
| 4,699,134 | 10/1987 | Samuelson . |
| 4,743,499 | 5/1988 | Volke . |
| 4,803,078 | 2/1989 | Sakai . |
| 4,856,502 | 8/1989 | Ersfeld et al. . |
| 4,950,291 | 8/1990 | Mulligan . |
| 4,960,116 | 10/1990 | Milner . |
| 5,019,210 | 5/1991 | Chou et al. . |
| 5,028,292 | 7/1991 | Incremona et al. . |
| 5,063,063 | 11/1991 | Miller . |
| 5,103,812 | 4/1992 | Salamone et al. . |
| 5,112,640 | 5/1992 | Warunek et al. . |
| 5,114,794 | 5/1992 | Sudo et al. . |
| 5,124,173 | 6/1992 | Uchiyama et al. . |
| 5,156,601 | 10/1992 | Lorenz et al. . |
| 5,178,726 | 1/1993 | Yu et al. . |
| 5,198,033 | 3/1993 | Kelley et al. . |
| 5,332,625 | 7/1994 | Dunn et al. . |

OTHER PUBLICATIONS

S.R. Gaboury and M.W. Urban, Quantitative analysis of the Si–H groups formed on poly(dimethylsiloxane) surfaces: an ATR FTi.r.approach, Polymer, vol. 33, No. 23, (1992), pp. 5085–5088.

C–P Ho and H. Yasuda, Coatings and Surface Modification by Methane Plasma Polymerization, J. Applied Polymer Science, vol. 39, (1990), pp. 1541–1552.

P.M. Triolo and J.D. Andrade, Surface modifiction and characterization of some commonly used catheter materials. II. Friction characterization, J. Biomedical Materials Research, vol. 17, (1983), pp. 149–165.

S.L. Kaplan and P.W. Rose, Plasma Processes in the Plastics Industry, a paper presented at the RadTech'90–North America Conference Proceedings in Chicago, Illinois, Mar. 25–29, 1990, 3 pages.

R. Cormia and O.Kolluri, Use Plasmas To Re–engineer Your Advanced Materials, Research & Development, Jul. 1990, Cahners Publishing Co., 5 pages.

S.L. Kaplan, Gas Plasma Deposition of High Barrier Polymer Coatings, Technical Notes from HIMONT/Plasma Science, Foster City, California, Copyright, Plasma Science, Inc., Oct. 1989, No. 6, pp. 1–4.

O.S. Kolluri et al., Plasma Assisted Coatings for the Plastics Industry, paper presented at the Fourth International Conference on Surface Modification Technologies, Nov. 1990, Paris, France, Technical Notes from HIMONT/Plasma Science, Foster, California, pp. 1–8.

E. M. Liston, Plasma Treatment for Improved Bonding: A Review, J. Adhesion, (1989), vol. 30, pp. 199–218.

S.L. Kaplan and P.W. Rose, Plasma Surface Treatment of Plastics to Enhance Adhesion: An Overview, CopyrightHIMONT/Plasma Science, Foster City, California, Jul. 1991, 5 pages.

Plasma Progress, Permanency of Plasma Surface Chemical Modification, HIMONT/Plasma Science, Issue 2, Mar., 1993, pp. 1–4.

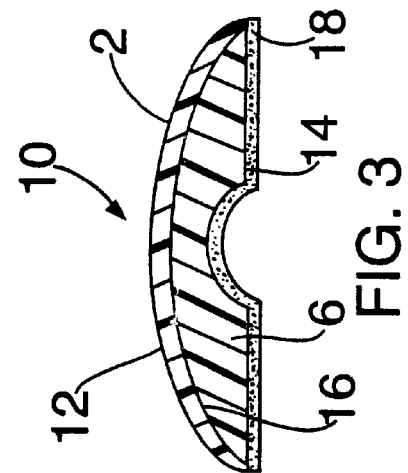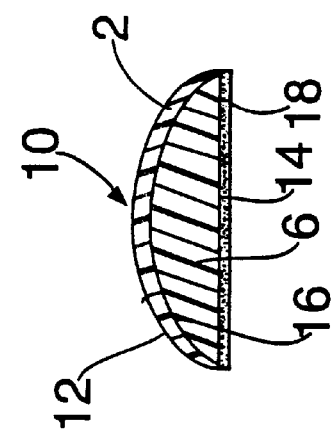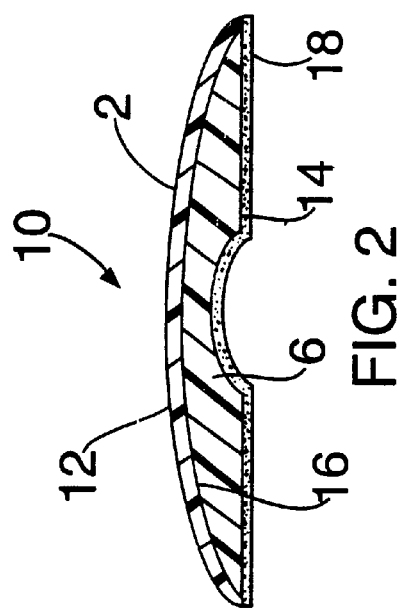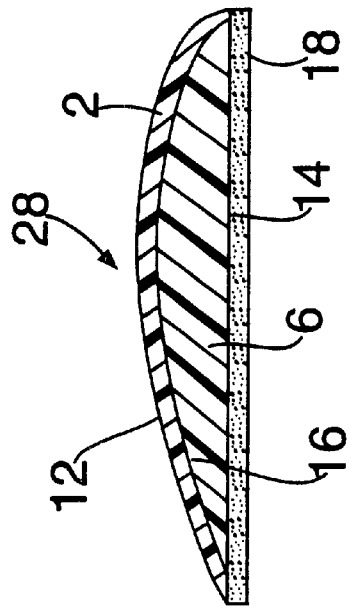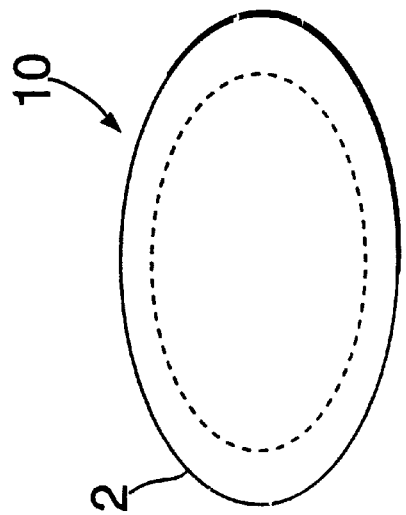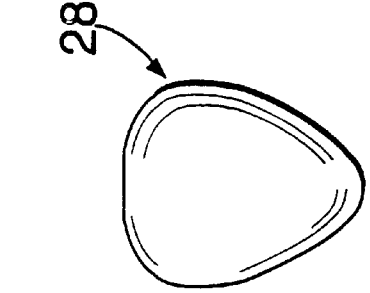

SOFT POLYSILOXANES HAVING A PRESSURE SENSITIVE ADHESIVE

CROSS REFERENCE TO RELATED APPLICATIONS

This application is a continuation of International Application No. PCT/US94/14164, filed Dec. 19, 1994 and designating the United States, which PCT application is in turn a continuation-in-part of U.S. application Ser. No. 08/171,799, filed Dec. 22, 1993, abandoned, the benefit of which applications are claimed pursuant to the provisions of 35 U.S.C. 120, 363 and 365(C). The invention of the present application is related to the invention disclosed in PCT/US93/06111.

BACKGROUND

International Application No. PCT/US 93/06111 titled "Method and Device for Cushioning Limbs" discloses a novel polysiloxane elastomer useful for cushioning limbs, ie. toes and fingers, or other body parts, ie. bunions. The elastomer is characterized as being very soft, ie. having a low durometer, and as also having an inherent self-tackiness. This self-tackiness is useful for securing the elastomeric cushion to a limb. However, it was found that in certain situations, ie. topical corns and calluses, the self-tack of the elastomer was not sufficient to hold the elastomeric cushion in place for extended periods of time. Efforts were then made to provide an article made of the soft, polysiloxane elastomer having a pressure sensitive adhesive on at least one of its surfaces, in order to adhere the cushioning article to the afflicted area more effectively. Polysiloxanes, or silicone materials are generally considered difficult to bond with adhesives due to very low surface energy. Therefore, an exhaustive search was initiated for bondable adhesives, liquid primers, adhesive tie coats, and processes that could surface modify polysiloxanes, particularly those described in International Application No. PCT/US 93/06111. A class of adhesives which were focused on early in the development cycle were silicone adhesives. However, although silicone adhesives typically bonded well to polysiloxanes, they performed poorly when used for adhering an article to an afflicted limb. Liquid primers demonstrated a high failure rate. The focus then shifted to acrylic adhesives with the addition of a tie coat or auxiliary surface modification process to enhance bondability to the polysiloxane surface. The use of primers or tiecoats proved to be unsuccessful because the adhesive either bonded poorly to the polysiloxane or delaminated over time. Therefore, further research efforts were undertaken to discover a process for enhancing bondability of a pressure sensitive adhesive to the soft, polysiloxane elastomer. The use of a pressure sensitive adhesive would allow the polysiloxane elastomeric cushion to adhere to the limb in situations where the inherent tackiness of the polysiloxane was insufficient to hold the elastomeric cushion in place for extended periods of time.

SUMMARY OF THE INVENTION

The present invention is directed towards an article comprising a soft polysiloxane elastomer having a pressure sensitive adhesive on at least one surface of the elastomer, wherein the polysiloxane elastomer is prepared by curing an organopolysiloxane composition comprising:

(i) a vinyl-containing high viscosity organopolysiloxane or a blend of high viscosity vinyl-containing organopolysiloxanes;

(ii) a low viscosity organopolysiloxane and a blend of low viscosity organopolysiloxanes;

(iii) a reinforcing filler;

(iv) a platinum catalyst; and (v) a hydrogen containing polysiloxane copolymer wherein the molar ratio of hydrogen to vinyl radicals in the total composition is less than 1.2, such that after curing, the degree to which the soft, polysiloxane elastomer is partially crosslinked is 30 to 90%;

wherein the soft polysiloxane elastomer is characterized as having:

a hardness of 5–55 durometer units (Shore 00), a tensile strength of 0.14–5.52 mega Pascals (20–800 pounds/square inch), a minimum elongation of 250–1100 percent and a tear strength of 0.88–35.2 kN/m (5–200 pound/inch).

In another embodiment, the soft polysiloxane elastomer is further characterized as having:

a hardness of 15–45 durometer units (Shore 00), preferably 20–35 units, a tensile strength of 0.35–5.52 mega Pascals (50–800 pounds/square inch), a minimum elongation of 350–800 percent and a tear strength of 1.22–26.4 kN/m (7–150 pound/inch).

In another embodiment, the present invention is directed towards an article comprising a soft polysiloxane elastomer having a pressure sensitive adhesive on at least one surface of the elastomer, wherein the polysiloxane elastomer is prepared by curing an organopolysiloxane composition comprising, based upon 100 parts total composition:

(i) 20 to 90 parts of a vinyl-containing high viscosity organopolysiloxane or a blend of high viscosity vinyl-containing organopolysiloxanes having no more than 25 mole percent of phenyl radicals and having a viscosity of 2,000 to 1,000,000 centipoise at 25° C. of the formula:

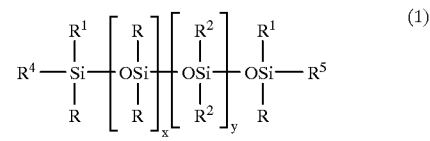

where $R^1$ is selected from the class consisting of alkenyl, alkyl and aryl radicals and R is a monovalent hydrocarbon radical, $R^2$ is selected from the class consisting of alkyl and aryl radicals, $R^4$ and $R^5$ are independently selected from the class consisting of alkyl and vinyl radicals; x varies from zero to 3000, preferably from 50 to 1000; and y varies from 0 to 300, preferably from zero to 50;

(ii) from 5 to 40 parts of a polymer selected from the class consisting of a low viscosity organopolysiloxane and a blend of low viscosity organopolysiloxanes having viscosity that varies from 20 to 5,000 centipoise at 25° C. and having no more than 25 mole percent phenyl radicals of the formula

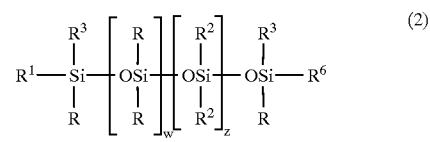

wherein $R^1$ and $R^6$ are independently selected from the class consisting of alkenyl, alkyl and aryl radicals, $R^2$ and R are as previously defined, $R^3$ is selected from the class consisting of alkyl, aryl and alkenyl radicals, w varies from 0 to 500, preferably from zero to 300, and z varies from 0 to 200, preferably from zero to 50;

(iii) from 10 to 70 parts of a reinforcing filler;

(iv) from 0.1 to 50 parts per million of platinum catalyst (as platinum metal) to the total composition; and (v) from 0.1 to 50 parts of a hydrogen containing polysiloxane copolymer wherein the molar ratio of hydrogen to alkenyl radicals in the total uncured composition is less than 1.2, such that after curing, the degree to which the soft polysiloxane elastomer is partially crosslinked is 30 to 90%. Preferably, the ratio of hydrogens to alkenyl radicals in the composition is about 0.5 to 1.2. Preferred is that the silica is employed in amounts ranging about 15 to about 40 parts per 100 parts of the uncured composition. Also preferred is that the reinforcing filler is silazane treated silica, precipitated silica, fumed silica or mixtures thereof.

The pressure sensitive adhesive can have a peel strength of 0.33–4.93 kN/m (30–450 oz/in), a tack of 50–1000 grams or a shear strength of 10–3000 minutes. Preferably the pressure sensitive adhesive employed with the soft, polysiloxane elastomers is an acrylic-based adhesive.

In another embodiment, at least one surface of the soft, polysiloxane elastomer, other than the surface having the pressure sensitive adhesive, is bonded to a topcover, preferably a topcover which is also a polysiloxane elastomer. The article containing the polysiloxane elastomer can be formed into sheet padding, a finger pad, a corn pad, a callus pad, a blister pad, a heel pad or a toe pad.

In another embodiment, the present invention is directed towards a method for cushioning a limb, comprising contacting the limb with the article made of the soft, polysiloxane elastomer having a pressure sensitive adhesive on at least one surface of the elastomer.

In another embodiment, the present invention is directed towards a process for preparing the cushioning article comprising a) treating at least one surface of the cured polysiloxane elastomer with a low temperature gaseous plasma for a time effective to modify the surface of the polysiloxane elastomer for accepting the pressure sensitive adhesive; and b) applying the pressure sensitive adhesive to said modified surface. The low temperature gaseous plasma can be argon, nitrous oxide, oxygen, purified air, carbon dioxide, hydrogen or mixtures thereof.

One advantage of the present invention is that it provides an article containing a soft, polysiloxane elastomer having a hardness of about 5–55 durometer units (Shore 00) and also having a pressure sensitive adhesive which will adhere the article to a limb more securely than can be provided by the inherent tack of the polysiloxane.

A second advantage of the present invention is that it provides an article containing a soft polysiloxane elastomer having a pressure sensitive adhesive and a method for relieving limb discomfort by the use of said article, through reduction of pressure and friction on the limb.

A third advantage of the present invention is that it provides an article containing a soft, polysiloxane elastomer having a pressure sensitive adhesive, for relieving limb discomfort, where the polysiloxane elastomer can be economically produced using injection molding or extrusion technologies.

A fourth advantage of the present invention is that it provides a process for bonding a pressure sensitive adhesive to a soft, polysiloxane elastomer, where the process leaves the elastomeric properties of the polysiloxane substantially unchanged, with the exception of the modification of the surface for accepting the pressure sensitive adhesive.

A fifth advantage of the present invention is that it provides a process for bonding a pressure sensitive adhesive to a soft, polysiloxane elastomer, where the process is environmentally safe or even safer than other known processes for bonding pressure senstive adhesives to polysiloxanes.

A sixth advantage of the present invention is that it provides a process for bonding a pressure sensitive adhesive to a soft, polysiloxane elastomer, where the process is repeatable, reliable and as economically efficient or even more so than other known processes.

BRIEF DESCRIPTION OF THE DRAWINGS

FIG. 1 is a perimeter view of corn pad 10.

FIG. 2 is a cross sectional side view of corn pad 10.

FIG. 3 is a cross sectional front view of corn pad 10.

FIG. 4 is a perimeter view of callus pad 28.

FIG. 5 is a cross sectional side view of a callus pad 28.

FIG. 6 is a cross-sectional front view of callus pad 28.

IN THE FIGURES

Refering to the drawings corn pad 10 of FIGS. 1, 2 and 3 and callus pad 28 of FIGS. 4, 5 and 7 share the following common characteristics: they are all articles comprised of topcover 2, a soft, cushioning polysiloxane layer 6 and pressure sensitive adhesive 18. Topcover 2 typically has a smooth exterior surface 12 and an interior surface 16. Soft, cushioning polysiloxane layer 6 is bonded to interior surface 16 of topcover 2. Cushioning layer 6 can be of either uniform or non-uniform thickness, with a surface 14 bonded to pressure sensitive adhesive 18. Pressure sensitive adhesive 18 allows the article to have greater adhesive properties, ie greater tack, than the inherent tack of cushioning polysiloxane layer 6.

DETAILED DESCRIPTION OF THE INVENTION

The term "alkyl" refers to radicals having from 1 to 8 carbon atoms per alkyl group, such as methyl, ethyl, propyl, butyl, pentyl, hexyl, octyl and the like.

The term "alkenyl" refers to radicals having from 2 to 8 carbon atoms such as, vinyl, allyl and 1-propenyl.

The term "aryl" refers to mononuclear and binuclear aryl radicals such as, phenyl, tolyl, xylyl, naphthyl and the like; mononuclear aryl alkyl radicals having from zero (ie. no alkyl group or a bond) to 8 carbon atoms per alkyl group such as benzyl, phenyl and the like.

The term "monovalent hydrocarbon radicals" includes hydrocarbon radicals such as alkyl, alkenyl and aryl.

The term "article" includes devices containing the polysiloxane elastomer having a pressure sensitive adhesive, which can be applied either to a limb or to footwear.

It should be recognized that the soft, polysiloxane cushioning layer possesses tack properties throughout its entire cushioning layer (ie. the interior). However, surface tack can be modified to be greater than or less than the interior tack, or the surface tack can even be eliminated so there is no tack, in order that the modified polysiloxane surface can receive the pressure sensitive adhesive. Quantitative measurements of tackiness for either the adhesive or the soft, polysiloxane cushioning layer can be made using a suitable tack tester, such as a Polyken® probe tack tester, a rolling ball tack tester, a peel tester or combinations thereof. Tack can be tested with the Polyken® probe tester in accordance with any suitable procedure, such as American Society For Testing and Materials (ASTM) Designation: D2979-71 (Reapproved 1982), Standard Test Method for Pressure-Sensitive Tack of Adhesives Using an Inverted Probe Machine, pp. 187–189, from the Annual Book of ASTM Standards, Vol. 15.09. The Polyken® probe tack tester is the trademark of the Kendall Company, under license by Testing Machines Inc., Mineola, Long Island, N.Y. Tack can also be tested with a rolling ball tack tester in accordance with Pressure Sensitive Tape Council, Test Methods for Pressure Sensitive Tapes, 10th Edition, PSTC-6, revised Aug., 1989, pp. 33–34 or ASTM D3121. Tack can also be tested with a peel tester in accordance with Pressure Sensitive Tape Council, Test Methods for Pressure Sensitive Tapes, 10th Edition, PSTC-1, revised August 1989, pp. 23–24. The soft, cushioning layer can be artificially aged prior to tack testing using conventional accelerating aging procedures, such as by exposing the layer to ultraviolet light, elevated temperatures and/or elevated humidity. The term "limb" refers to the paired appendages of the body used especially for movement or grasping, including the legs, knees, shins, ankles, feet, toes, arms, elbows, forearms, wrists, hands, fingers or any part thereof.

The term "cushioning" means that the soft, cushioning layer protects the limb against forces or shocks.

The term "curing" refers to any process by which the raw or uncured polysiloxanes containing reinforcing agents are converted to the soft, partially crosslinked, reinforced polysiloxane elastomer. Such curing can be achieved by increasing the molecular weight of the uncured polysiloxane elastomers to the extent desired through crosslinking, using heating or standing at ambient, as described U.S. Pat. No. 3,445,420. Generally, the degree to which the uncured polysiloxane composition can be partially crosslinked can range from about 30 to about 90%, based upon the alkenyl-containing polysiloxane, more preferably from about 50 to about 90%.

The article can be prepared by bonding a layer of the soft, polysiloxane elastomer onto a topcover or elastomer sheet using techniques such as compression molding, liquid injection molding, transfer molding, casting and the like, followed by application of the pressure sensitive adhesive.

The optional topcover of the article can be made of high tear strength silicone elastomers such as taught in U.S. Pat. Nos. 3,445,420 and 4,162,243. Other suitable topcovers can include silicone films, polymeric coatings such as silicone dispersed in xylene, as described in U.S. Pat. No. 3,884,866, coated textile materials or other compatible polymers such as polyurethane or polyvinyl chloride (pvc) films. The topcover can be a single material or laminates of several materials.

The soft, polysiloxane elastomer can be formed by curing a mixture of a alkenyl-functional polysiloxanes, such as a vinyl containing polysiloxane, and a hydrogen containing polysiloxane containing active hydrogen groups. In this regard, the term "hydrogen" refers to active hydrogens which are directly bonded to a silicon atom (Si—H), for example, silicon hydrides and hydrogen containing organopolysiloxanes. Such amounts of the hydrogen containing polysiloxane will be dependent upon factors such as the molar ratio of alkenyl radicals to active hydrogens in the uncured composition and the nature of these components, including such variables as polymer chain length, molecular weight and polymer structure. In its examples, U.S. Pat. No. 3,884,866, discloses organopolysiloxane elastomers having a ratio of hydrogen to vinyl of about 2:1 and which are significantly harder than the present organopolysiloxane elastomers. The organopolysiloxane elastomers employed in the present invention, prior to curing, have a ratio of hydrogens to alkenyl radicals of less than 1.2, preferably 0.5 to 1.2.

Determinations of the hardness of the topcover and of the soft, cushioning layer can be made with any suitable durometer for testing hardness. One test method entails resting the edge of a Shore 00 durometer on a material, applying a presser foot to the material without shock and taking the average of three readings. Further details for testing hardness can be found in ASTM Test Method D2240. One of ordinary skill in the art will appreciate that elastomers measured by the Shore 00 durometer scale are softer than those measured by the Shore A durometer scale. The elastomers employed in the present invention are signicantly softer than those taught in U.S. Pat. No. 3,844,866.

Representative vinyl-containing high viscosity organopolysiloxanes of (1) suitable for preparing a base material include, but are not limited to the following.

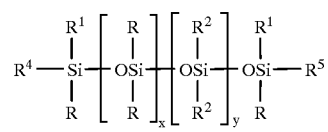

(1)

| Polymer | R | $R^1$ | $R^2$ | $R^4$ | $R^5$ | x | y |
|---|---|---|---|---|---|---|---|
| 1 | —$CH_3$ | —$CH_3$ | —$C_6H_5$ | —$CH_3$ | —$C_2H_3$ | 925 | 50 |
| 2 | —$CH_3$ | —$CH_3$ | —$C_6H_5$ | —$C_2H_3$ | —$C_2H_3$ | 809 | 45 |
| 3 | —$CH_3$ | —$CH_3$ | —$C_6H_5$ | —$C_2H_3$ | —$C_2H_3$ | 611 | 41 |
| 4 | —$CH_3$ | —$CH_3$ | —$C_6H_5$ | —$C_2H_3$ | —$C_2H_5$ | 471 | 30 |
| 5 | —$CH_3$ | —$CH_3$ | —$CH_3$ | —$C_2H_3$ | —$CH_3$ | 600 | 20 |
| 6 | —$CH_3$ | —$CH_3$ | —$CH_3$ | —$C_2H_3$ | —$C_2H_5$ | 800 | 40 |
| 7 | —$CH_3$ | —$CH_3$ | —$CH_3$ | —$C_2H_3$ | —$C_2H_3$ | 600 | 20 |
| 8 | —$CH_3$ | —$CH_3$ | —$CH_3$ | —$C_2H_3$ | —$C_2H_3$ | 800 | 40 |

Representative low viscosity organopolysiloxanes of formula (2) suitable for use in preparing a base material include, but are not limited to the following.

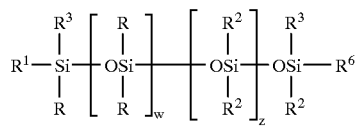

(2)

| Polymer | R | $R^1$ | $R^2$ | $R^3$ | $R^6$ | w | z |
|---|---|---|---|---|---|---|---|
| 1 | —$CH_3$ | —$C_2H_3$ | —$C_6H_5$ | —$CH_3$ | —$CH_3$ | 138 | 13 |
| 2 | —$CH_3$ | —$C_2H_3$ | —$C_6H_5$ | —$CH_3$ | —$CH_3$ | 192 | 39 |
| 3 | —$CH_3$ | —$C_2H_3$ | —$CH_3$ | —$CH_3$ | —$CH_3$ | 125 | 25 |
| 4 | —$CH_3$ | —$C_2H_3$ | —$CH_3$ | —$CH_3$ | —$CH_3$ | 90 | 20 |
| 5 | —$CH_3$ | —$CH_3$ | —$CH_3$ | —$CH_3$ | —$CH_3$ | 125 | 25 |

The base material prepared from the vinyl-containing high viscosity organopolysiloxanes of formula (1) and the low viscosity organopolysiloxanes of formula (2) can be admixed with a polysiloxane containing dimethyl and methyl hydrogen siloxanes. The amount of hydrogen-containing organopolysiloxane used should be sufficient to achieve a ratio of alkenyl radicals to hydrogen in the uncured composition of less than 1.2.

The ratio of the thicknesses of the soft, cushioning layer to the topcover or the sheet elastomer can range from about 1:1 to about 100:1, preferably about 5 to 60:1; more preferably about 10 to 30:1.

The polysiloxane elastomers are reinforced with a suitable reinforcing agent or filler such as titanium dioxide, calcium carbonate, lithopone, zinc oxide, zirconium silicate, silica aerogel, iron oxide, diatomaceous earth, silazane-treated silica, precipitated silica, fumed silica, mined silica, glass fibers, magnesium oxide, chromic oxide, zirconium oxide, aluminum oxide, alpha quartz, calcined clay and the like, as well as various reinforcing silica fillers taught in U.S. Pat. No. 3,635,743, preferably silazane treated silica, precipitated silica, fumed silica or mixtures of any of the above. Preferably the reinforcing filler is a fumed silica with a surface area ranging from about 80 to about 400 square meters/gram ($m^2$/g), preferably from about 200 to about 400 $m^2$/g. Typically the reinforcing agent is mixed with the vinyl-containing high viscosity organopolysiloxanes (1) and low viscosity organopolysiloxane (2) prior to addtion of the hydrogen containing polysiloxane. The reinforcing filler can be employed in the uncured composition in an amount ranging from 10 to about 70 parts per 100 parts of the uncured composition, preferably from 15 to about 40 parts, more preferably from about 20 to about 30 parts. In the cured soft, polysiloxane layer, such amounts correspond to about ten to about 70% by weight, preferably from about 15 to about 40%, more preferably from about 20 to about 30%.

Preferably, the durometer or hardness of the soft polysiloxane elastomers of the present invention can be lowered (ie. made softer) by incorporating low viscosity polysiloxanes into the uncured composition. Representative low viscosity polysiloxanes include polydimethylsiloxane fluids or vinyl-containing polydimethylsiloxane fluids. The molecular weight average of the plasticizer can range from about 750 to about 30,000. The low viscosity polysiloxanes can be employed in an amount ranging from about zero to about 50% by weight of the uncured composition, preferably from about 10 to about 30%.

The polysiloxane elastomers of the present invention are further distinguished from known polysiloxane compositions. Such known polysiloxane compositions lack the requisite hardness, tensile strength, elongation and/or tear strength characteristic of Applicants' polysiloxane elastomers, as based upon standard elastic materials testing. For example, unreinforced polysiloxane compositions such as those taught in U.S. Pat. Nos. 3,363,973, 3,548,420, 4,019,209 must be enclosed in an envelope or other supporting means, ie. foam impregnation, in order to maintain the shape or durability of an article derived from such compositions. Further, U.S. Pat. No. 4,573,216 teaches impact dissipators in which a polysiloxane viscous-like fluid having an exposed surface is not fully enclosed and is also attached to a supporting structure. However, such polysiloxane viscous-like fluids are not viscoelastic and lack measurable hardness, tensile strength, elongation and/or tear strength. In contrast, Applicants' soft, polysiloxane cushioning layer is viscoelastic and has a measurable hardness, tensile strength, elongation and/or tear strength as per ASTM methods 624-86 and D-412-87.

Further, the soft, polysiloxane elastomers of the present invention can retain their elastic properties after prolonged action of compressive stresses, a property known as compression set. Compression set is an indicator of durability. According to ASTM Designation: D395-85, Standard Test Methods for Rubber Property-Compression Set, pp. 34–35, the actual stressing service may involve the maintenance of a definite deflection, the constant application of a known force, or the rapidly repeated deformation and recovery resulting from intermittent compressive forces. Though the latter dynamic stressing, like the others, produces compression set, its effects as a whole are simulated more closely by compression flexing or hysteresis tests. Therefore, compression set tests are considered to be mainly applicable to service conditions involving static stresses. Tests are frequently conducted at elevated temperatures. In a first method utilizing static stresses, a test specimen is compressed to a deflection and maintained under this condition for a specified time and at a specified temperature. In a second method utilizing static stresses, a specified force is maintained under this condition for a specified time and at a specified temperature. After application of the specified deflection or specified force the residual deformation of a test specimen is measured 30 minutes after removal from a suitable compression device in which the specimen has been subjected for a definite time to compressive deformation under specified conditions. After measurement of the residual deformation, the compression set as specified in the appropriate method is calculated according to ASTMD395-85 equations.

The term "pressure sensitive adhesive" as used herein, refers to adhesives which, in dry form, are permanently tacky at room temperature and firmly adhere to surfaces upon mere contact, according to the Encyclopedia of Polymer Science and Engineering, Vol. 1, John Wiley & Sons, New York, (1985), p. 551. Such pressure sensitive adhesives differ from the soft polysiloxane elastomers disclosed herein, in that they are not inherent to the polysiloxanes and thus, must be applied separately. Further, such pressure sensitive adhesives tend to have greater adhesive properties, ie greater tack, than the inherent tack of polysiloxanes disclosed herein. The pressure sensitive adhesive should be strong enough to hold the soft polysiloxane article to a limb, for about 8 hours to 48 hours or more. The pressure sensitive adhesive should also be able to meet the peel, tack, and shear test requirements as described in table 1. It should be appreciated that one of ordinary skill in the art could utilize these methods to test the physical properties of a pressure senstive adhesive. Also, it would be desirable that the pressure sensitive adhesive is bonded to the soft polysiloxane elastomer so there is minimal adhesive delamination from the article. Delamination refers to a failure mode where an adhesive splits away from an article to which it is bonded, because of its failure to adhere to the article. Generally the thickness of an adhesive applied to the polysiloxane elastomer can range from about one to about 20 mils (dry), preferably from about 2 to about 8 mils.

Pressure sensitive adhesives which can be employed for bonding to the soft, elastomeric article of polysiloxane disclosed herein include, but are not limited to the following:

A. Solvent-based acrylic adhesives such as:
Monsanto GMS 737, trademark of Monsanto Corporation, St. Louis, Mo.;
National Starch Durotak 72-9720 and 80-1197, trademark of National Starch & Chemical Corp., Bridgewater, N.J.
Ashland's AROSET 1113-AD-40 and 1085-Z-45, trademark of Ashland Oil Co., Ashland, Ky.

B. Solvent-based rubber adhesives such as:
National Starch 36-6172
Hauthaway 59-133, trademark of C. L. Hauthaway, Lynn, Mass.

C. Acrylic emulsion adhesives such as:
  Monsanto GME 2397
  Rohm & Haas N580, trademark of Rohm & Haas Co., Philadelphia, Pa.
  Unocal 76 RES 9646, trademark of Unocal Corp., Los Angeles, Calif.;
  Ashland's AROSET 2022-W-50
D. Adhesive Transfer Tapes such as:
  3M F-9465 PC, trademark of 3M Co., St. Paul, Minn.
  Avery-Denison MED 1116, trademark of Avery Denison Corp., Pasedena, Calif.
  ARCare 7530, trademark of Adhesive Research Inc., Glen Rock, Pa.; and
  RX230U, trademark of Coating Science Inc., Bloomfield, Conn.

Preferably the pressure sensitive adhesive is a sovent-based rubber or acrylic adhesive, more preferably Monsanto 737 modified with the addition of 1–50 parts per hundred resin (PHR) of Pentalyn H® tackifier.

A tackifier is any substance which enhances the property of tack of a pressure sensitive adhesive. Suitable tackifiers include rosin acid derivatives such as Pentalyn H of the Hercules Corporation, terpene based derivatives and synthetic C-5 tackifiers such as Escorez 1310 of the Exxon Corporation. The amount of tackifier in the adhesive can range from about 1 to about 60% by weight of the adhesive, preferably from about 5 to about 40%.

Plasmas, often dubbed "the fourth state of matter", are ionized gases that contain ions, electrons, radicals, excited molecules, and atoms which are generated by radio frequency (RF) or microwave produced glow discharges at reduced pressures (0.01–10 torr). Low-temperature gaseous plasma, is used to improve the wetability and bondability of polymers through surface modification. Enhanced wetability arises from the introduction of surface polar groups (e.g. carbonyls, carboxyls, and hydroxyls). Suitable gas plasmas which can be employed to prepare or pretreat the surface of the soft polysiloxane prior to application of the desired adhesive, include but are not limited to carbon dioxide, argon, oxygen, zero air, nitrous oxide, helium, carbon tetrafluoride, hydrogen or mixtures thereof. Suitable mixtures include oxygen/argon, helium/oxygen, zero air/argon, carbon tetrafluoride/hydrogen, carbon tetrafluoride/oxygen, preferably nitrous oxide/carbon dioxide and the like.

Plasma surface modification is controlled by essentially four factors: gas chemistry, gas flow rate, process time and energy level, ie. power. Gas chemistry relates to the selection of gases which can be employed to modify the surface chemistry of the polysiloxane. Gas flow rate is the amount of gas delivered during the treatment process. Process time relates to the length of time the soft, elastomeric article of polysiloxane is exposed to the gaseous plasma. Energy levels, ie. power, is the energy which is supplied to the gas to generate the plasma. Such factors tend to be instrument specific, based upon the design of the plasma modification equipment. Optimum conditions can be determined through experimental procedures by varying differing levels of each factor for each type of equipment.

Several physical and chemical tests can be performed to evaluate the effect that different gaseous plasmas have on modifying the surface of a polysiloxane elastomer for accepting a pressure sensitive adhesive. These tests include attenuated total reflectance fourier transform infrared spectroscopy (ATR-FTIR) analysis, surface energy determinations (contact angle/dyne pens), 180° peel test, shear strength test, polyken probe tack test (adhesive), aging studies and evaluation of adhesive failure mode such as delamination. For example, ATR-FTIR measures the surface modification by the gaseous plasma carried out on the polysiloxane elastomer prior to application of the adhesive.

After application of the adhesive to the polysiloxane elastomer, the 180° peel test, shear strength test, polyken Probe Tack test can be used to monitor the bondability of the adhesive with the plasma-modified surface of the polysiloxane through the use of accelerated aging studies. The 180° peel test can be performed as described in Pressure Sensitive Tape Council, Test Methods for Pressure Sensitive Tapes, 10th Edition, PSTC-1, revised August 1989, pp. 23–24. The shear test can be performed as described in PSTC-7, Pressure Sensitive Tape Council, Test Methods for Pressure Sensitive Tapes, 10th Edition, revised August 1989, pp. 35–37. Such methods can be slightly modified as needed, eg. instead of a pressure sensitive tape, the adhesive can be applied, prior to testing, to a substrate such as a polysiloxane elastomer, sheet or plaque.

Table 1 summarizes selected physical properties of components for preparing a cushioning article of the present invention.

| Table 2. | Topcover | Soft, cushioning Layer | Adhesive |
|---|---|---|---|
| HARDNESS | (polysiloxane) | (polysiloxane) | |
| durometer | 20–80 units (Shore A) | 5–55 units (Shore 00) | N/A |
| (preferred) | 45–55 | 15–45; 20–35 | |
| TENSILE STRENGTH | | | |
| lb/sq inch (psi) | 100–2,000 | 20–800 | N/A |
| (preferred) | 300–1500 | 50–800 | |
| Mega Pascals | 0.69–13.8 | 0.14–5.53 | |
| (preferred) | 2.07–10.35 | 0.35-5.53 | |
| MINIMUM ELONGATION | | | |
| percent | 100–1500 | 250–1100 | N/A |
| (preferred) | 300–800 | 350–800 | |
| TEAR STRENGTH | | | |
| lb/inch | 75–300 | 5–200 | N/A |
| (preferred) | 75–200 | 7–150 | |
| kN/m | 13.2–52.8 | 0.88–35.2 | |
| (preferred) | 13.2–35.2 | 1.22–26.4 | |
| POLYKEN PROBE TACK | | | |
| grams | not applicable | 10–450 | 50–1000 |
| (preferred) | not applicable | 50–250 | 100–600 |
| ROLLING BALL TACK | | | |
| inches | not applicable | 0–3 | N/A |
| (preferred) | not applicable | 0–2; 0–1 | N/A |
| centimeters | not applicable | 0–7.6 | N/A |
| (preferred) | not applicable | 0–5; 0–2.5 | N/A |
| PEEL STRENGTH TEST | | | |
| (lb/in) | not applicable | 0.02–80 | 30–450 oz/in |
| (preferred) | not applicable | 0.05–40 | 125–300/ (oz/in) |
| (kN/m) | not applicable | 0.004–14.08 | 0.33–4.93 |
| (preferred) | not applicable | 0.009–7.04 | 1.37–3.28 |
| COMPRESSION SET | | | N/A |
| percent | | | |
| SHEAR STRENGTH | | | |
| minutes | | | 10–3000 |
| (preferred) | | | 25–800 |

In above Table 1, for the adhesive, polyken probe tack tester is set at a dwell time = 1 second, speed = 1 centimeter per second. For the soft, cushioning layer, polyken probe tack tester is set at a dwell time = 20 seconds, speed = 5 centimeters per second.

EXAMPLE 1

Using a technique known as compression molding, to a mold cavity heated to 149° C. (300° F.) is dispensed one gram (g) of an elastomer mixture under the trade designation of Silastic 599-HC Liquid Silicone Rubber (Dow Corning, Midland, Mich.). This elastomeric mixture is prepared by combining 1:1 part A to part B of a 2-part addition cure silicone elastomer. A first topmold having a core complementary to the cavity is applied to the elastomer mixture, and the elastomer is cured for about one minute to yield a shell (polysiloxane elastomeric topcover). The first topmold is removed, leaving the resultant elastomeric shell in the cavity mold. About 9 g of an uncured, reinforced polysiloxane elastomer are added to the shell.

The uncured, reinforced polysiloxane elastomer is prepared from the following:

i) 61.0 parts of a high viscosity vinyl (Vi) containing organopolysiloxane of the formula

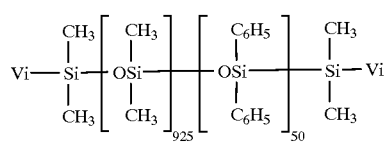

wherein such high viscosity vinyl containing organopolysiloxane (1) has a viscosity of 60,000 centipoise at 25° C.

ii) 15.2 parts of a blend of low viscosity organopolysiloxane (2) which blend has a resulting viscocity of 500 centipoise at 25° C. and in which the organopolysiloxane (2) comprises a mixture of compounds of the following formulas

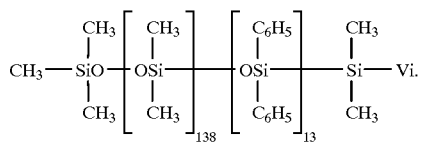

iii) 23.0 parts of silica reinforcing agent treated in the same manner as that disclosed in U.S. Pat. No. 3,635,743 iv) 6 parts per million platinum (0.02% platinum catayst containing 3% platinum metal) of a platinum complex such as that disclosed in U.S. Pat. No. 3,220,972 is added to a premixed base of i–iii)

v) 0.8 parts of a hydrogen-containing polysiloxane of the formula:

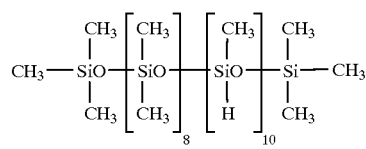

wherein the ratio of active hydrogens to vinyl in the uncured composition is about 0.8.

A second topmold having a core slightly smaller than that of the first topmold is applied to the reinforced elastomer to mold or bond the reinforced elastomer onto the elastomeric shell and cured for about two minutes at 137° C. to give a composite pad made of reinforced, soft tacky polysiloxane elastomer bonded to the polysiloxane elastomeric topcover or shell.

EXAMPLE 2

Using a technique known as compression molding, an unvulcanized silicone sheet is secured to a mold cavity. About 9 g of reinforced elastomer as described in Example 1 are added to the sheet. A topmold having a core slightly smaller than the cavity is applied to the reinforced elastomer to bond the elastomer onto the unvulcanized sheet. The sheet and the elastomer are cured for three minutes to vulcanize the sheet, giving a composite pad having a shell and a soft, cushioning layer bonded to the shell interior.

EXAMPLE 3

Essentially the same procedure of Example 1 is employed except that the reinforced elastomer is reformulated to 1:1 Component A to Component B.

EXAMPLE 4

Essentially the same procedure of Example 2 is employed except that the reinforced elastomer is reformulated to 1:1 Component A to Component B.

EXAMPLE 5

To a mold cavity heated to 75.5° C. (168° F.) is brushed an uncured dimethyl silicone elastomer dispersion in xylene (Item No. 40000, solids content 35%, available from Applied Silicone Corporation, Ventura, Calif.). The dispersion is allowed to flash for three minutes to begin to form a coating. About 9 g of reinforced elastomer as described in Example 3 are added to the coating in the cavity. A topmold having a core slightly smaller than the cavity is applied to the reinforced elastomer to bond the elastomer onto the coating, and the elastomer and coating are cured for 25 minutes at 177° C. (350° F.) to give the composite pad having a shell and a soft, cushioning layer bonded to the shell interior.

EXAMPLE 6

Using a technique known as liquid injection molding, a first topmold having a sprue hole (ie. injection port) is applied to cavity mold complementary to the first topmold, and both molds are heated to a temperature of 177° C. (350° F.). A mixture of the addition cure silicone elastomer of Example 1 (Applied Silicone LSR60 liquid silicone rubber) is injected into the mold parts via the sprue hole and cured for about one minute to form an elastomeric shell. The first topmold is removed and the elastomeric shell is removed from the first topmold. The elastomeric shell is placed into a mold cavity heated at 177° C. A second topmold having a sprue hole and a core slightly smaller than the first topmold is placed into the complementary mold cavity containing the shell. About 20 g of the reinforced elastomer of Example 3 is injected through the sprue hole into the cavity containing the shell and cured at 177° C. for one minute to give a composite pad.

EXAMPLE 7

Application of a pressure sensitive adhesive to the surface of a soft, elastomeric article of polysiloxane.

An untreated, soft, polysiloxane article is inserted into the plasma chamber of a Plasma Science PS0150E Surface Treatment System (Himont Plasma Sciences, Foster City, Calif.). The plasma system is programmed for desired treatment (i.e., gas, process time, gas flow and power) as described in Table 2. Argon is employed as the gas of choice. After removal of the article from the chamber, the soft, polysiloxane article receiving the plasma treatment is laminated with Monsanto 737 containing 10 PHR Pentalyn H, an acrylic-based pressure sensitive adhesive.

TABLE 2

| RUN | POWER (WATTS) | GAS FLOW (%) | TIME (MINUTES) | PEEL TEST (24 hr after bonding) (OZ/IN) | PEEL TEST (120 hr after bonding) (OZ/IN) |
|---|---|---|---|---|---|
| 1 | 148 | 23 | 3.25 | 150.4 ± 7.5 | 146.4 ± 27.2 |
| 2 | 20 | 2 | 0.50 | 146.0 ± 42.1 | 145.0 ± 24.1 |
| 3 | 20 | 2 | 6.00 | 156.1 ± 14.4 | 168.9 ± 29.6 |
| 4 | 275 | 44 | 0.50 | 119.7 ± 5.9 | 162.4 ± 24.4 |
| 5 | 20 | 44 | 6.00 | 157.4 ± 4.2 | 156.6 ± 13.5 |
| 6 | 148 | 23 | 3.25 | 167.7 ± 28.1 | 168.0 ± 37.2 |
| 7 | 275 | 44 | 6.00 | 176.5 ± 14.1 | 158.3 ± 15.2 |
| 8 | 275 | 2 | 0.50 | 131.8 ± 23.6 | 181.9 ± 39.7 |
| 9 | 20 | 44 | 0.50 | 33.1 ± 4.8 | 132.5 ± 12.5 |
| 10 | 275 | 2 | 6.00 | 14.2 ± 22.3 | 154.9 ± 27.3 |
| 11 | 148 | 23 | 3.25 | 140.0 ± 21.6 | 159.1 ± 14.6 |

We claim:

1. An article comprising a soft, polysiloxane elastomer having a pressure sensitive adhesive on at least one surface of the elastomer, wherein the polysiloxane elastomer is prepared by curing an organopolysiloxane composition comprising:
   (i) a vinyl-containing high viscosity organopolysiloxane or a blend of high viscosity vinyl-containing organopolysiloxanes;
   (ii) a low viscosity organopolysiloxane and a blend of low viscosity organopolysiloxanes;
   (iii) a reinforcing filler;
   (iv) a platinum catalyst; and
   (v) a hydrogen containing polysiloxane copolymer wherein the molar ratio of hydrogen to vinyl radicals in the total composition is less than 1.2, such that after curing, the degree to which the soft, polysiloxane elastomer is partially crosslinked is 30 to 90%;
wherein
   the soft polysiloxane elastomer is characterized as having:
      a hardness of 5–55 durometer units (Shore 00),
      a tensile strength of 0.14–5.52 mega Pascals (20–800 pounds/square inch),
      a minimum elongation of 250–1100 percent and
      a tear strength of 0.88–35.2 kN/m (5–200 pound/inch).

2. The article according to claim 1 wherein the soft polysiloxane elastomer is further characterized as having:
   a hardness of 15–45 durometer units (Shore 00), preferably 20–35 units,
   a tensile strength of 0.35–5.52 mega Pascals (50–800 pounds/square inch),
   a minimum elongation of 350–800 percent and
   a tear strength of 1.22–26.4 kN/m (7–150 pound/inch).

3. An article comprising a soft, polysiloxane elastomer having a pressure sensitive adhesive on at least one surface of the elastomer, wherein the polysiloxane elastomer is prepared by curing an organopolysiloxane composition comprising, based upon 100 parts total composition:
   (i) 20 to 90 parts of a vinyl-containing high viscosity organopolysiloxane or a blend of high viscosity vinyl-containing organopolysiloxanes having no more than 25 mole percent of phenyl radicals and having a viscosity of 2,000 to 1,000,000 centipoise at 25° C. of the formula:

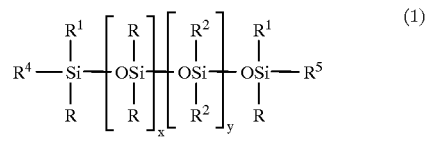

where $R^1$ is selected from the class consisting of alkenyl, alkyl and aryl radicals and R is a monovalent hydrocarbon radical, $R^2$ is selected from the class consisting of alkyl and aryl radicals, $R^4$ and $R^5$ are independently selected from the class consisting of alkyl and vinyl radicals; x varies from zero to 3000, preferably from 50 to 1000; and y varies from 0 to 300, preferably from zero to 50;

(ii) from 5 to 40 parts of a polymer selected from the class consisting of a low viscosity organopolysiloxane and a blend of low viscosity organopolysiloxanes having viscosity that varies from 20 to 5,000 centipoise at 25° C. and having no more than 25 mole percent phenyl radicals of the formula

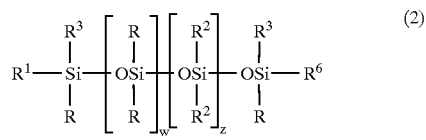

wherein $R^1$ and $R^6$ are independently selected from the class consisting of alkenyl, alkyl and aryl radicals, $R^2$ and R are as previously defined, $R^3$ is selected from the class consisting of alkyl, aryl and alkenyl radicals, w varies from 0 to 500, preferably from zero to 300, and z varies from 0 to 200, preferably from zero to 50;

(iii) from 10 to 70 parts of a reinforcing filler;
   (iv) from 0.1 to 50 parts per million of platinum catalyst (as platinum metal) to the total composition; and
   (v) from 0.1 to 50 parts of a hydrogen containing polysiloxane copolymer wherein the molar ratio of hydrogen to alkenyl radicals in the total uncured composition is less than 1.2, such that after curing, the degree to which the soft polysiloxane elastomer is partially crosslinked is 30 to 90%.

4. The article according to claim 3 wherein prior to curing, the ratio of hydrogens to alkenyl radicals in the organopolysiloxane composition is about 0.5 to 1.2.

5. The article according to claim 3 wherein the reinforcing filler is an amount ranging about 15 to about 40 parts per 100 parts of the uncured composition.

6. The article according to claim 3 wherein the the reinforcing filler is silazane treated silica, precipitated silica, fumed silica or mixtures thereof.

7. The article according to claim 1 wherein the pressure sensitive adhesive has peel strength of 30–450 (oz/in), a tack of 50–1000 grams or a shear strength of 10–3000 minutes.

8. The article according to claim 1 wherein the pressure sensitive adhesive is a solvent-based rubber or acrylic adhesive.

9. The article according to claim 1 wherein the soft polysiloxane elastomer is bonded to a topcover, preferably a topcover which is also a polysiloxane elastomer.

10. The article according to claim 9 which is sheet padding, a finger pad, a corn pad, a callus pad, a blister pad, a heel pad or a toe pad.

* * * * *